United States Patent [19]

Drobish et al.

[11] 4,304,226
[45] Dec. 8, 1981

[54] VAGINAL CONTRACEPTIVE

[75] Inventors: James L. Drobish, Wyoming; Thomas W. Gougeon, Springfield Township, Hamilton County, both of Ohio

[73] Assignee: The Procter & Gamble Company, Cincinnati, Ohio

[21] Appl. No.: 126,766

[22] Filed: Mar. 3, 1980

[51] Int. Cl.$^3$ .......................... A61F 5/46; A61M 7/00
[52] U.S. Cl. ................................ 128/127; 128/260
[58] Field of Search ........................ 128/127–130, 128/260

[56] References Cited

U.S. PATENT DOCUMENTS

| | | | |
|---|---|---|---|
| 2,580,133 | 12/1951 | Sheen | 128/127 |
| 2,697,057 | 12/1954 | Senger et al. | |
| 3,015,598 | 1/1962 | Jones | |
| 3,117,573 | 1/1964 | Snell | 128/127 |
| 3,279,996 | 10/1966 | Long, Jr. et al. | 128/260 |
| 3,416,530 | 12/1968 | Ness | 128/260 |
| 3,618,604 | 11/1971 | Ness | 128/260 |
| 3,683,904 | 8/1972 | Forster | 128/127 |
| 3,828,777 | 8/1974 | Ness | 128/260 |
| 3,832,252 | 8/1974 | Higuchi et al. | |
| 3,845,766 | 11/1974 | Zöller | 128/285 |
| 3,971,367 | 7/1976 | Zaffaroni | 128/260 |
| 3,983,874 | 10/1976 | Davis et al. | 128/285 |
| 3,991,760 | 11/1976 | Drobish et al. | 128/260 |
| 3,993,073 | 11/1976 | Zaffaroni | 128/260 |
| 3,995,633 | 12/1976 | Gougeon | 128/260 |
| 3,995,634 | 12/1976 | Drobish | 128/260 |
| 4,012,497 | 3/1977 | Schopflin | 128/130 |
| 4,016,251 | 4/1977 | Higuchi et al. | 128/130 |
| 4,067,961 | 1/1978 | Laughlin | |
| 4,145,408 | 3/1979 | Laughlin | |
| 4,198,976 | 4/1980 | Drobish et al. | 128/260 |
| 4,200,090 | 4/1980 | Drobish | 128/127 |

FOREIGN PATENT DOCUMENTS 21588 of 1897 United Kingdom .

Primary Examiner—C. Fred Rosenbaum
Attorney, Agent, or Firm—Donald E. Hasse; Michael J. Roth; Jack D. Schaeffer

[57] ABSTRACT

Improved reinforced devices, which can be retained in the vagina during intercourse, deliver spermicidal surfactants and provide contraceptive benefits. Lobed devices provide channels through which menses and other biological fluids can pass. Multi-compartment devices provide added protection against leakage, rupture or perforation during manufacture, handling and use.

20 Claims, 9 Drawing Figures

U.S. Patent   Dec. 8, 1981   Sheet 1 of 3   4,304,226
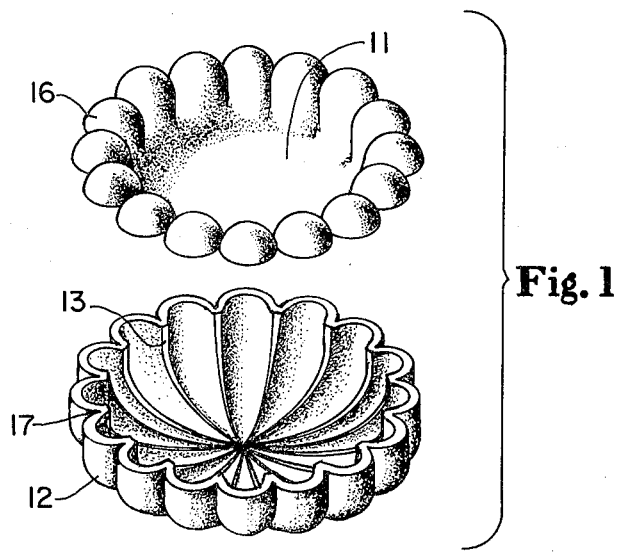
Fig. 1
Fig. 2
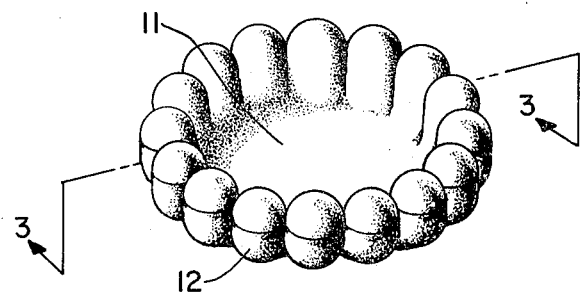
Fig. 3
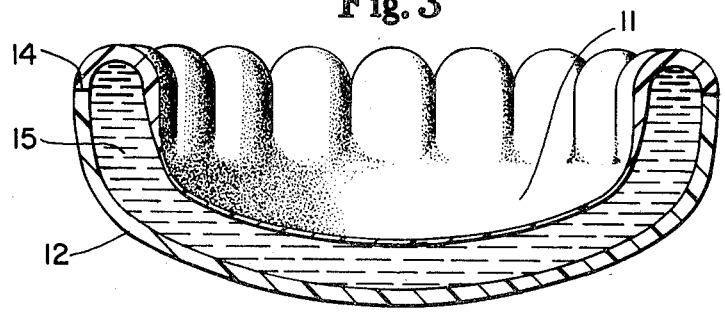

VAGINAL CONTRACEPTIVE

TECHNICAL FIELD

The present invention encompasses devices which are used in the vagina to deliver spermicidal surfactants. By virtue of their unique construction and shape, the devices herein are foldable for easy insertion. Once in position at or near the cervical os, the devices open to cap or block the os and remain in position, even during intercourse, so that access of the spermicidal surfactant source to the cervical os is not interrupted.

The devices of this invention are designed for use in the vagina, can be inserted by the user, and do not require insertion by a physician as, for example, in the case of intrauterine contraceptive devices. The devices are designed to remain in the vagina during the time between menstrual periods to provide desirable, prolonged release of a spermicidal surfactant, and their construction and shape facilitate retention therein. An effective between-period contraceptive device is thereby provided.

The devices of the present invention combine the desirable features of devices which provide prolonged release of medicaments, e.g., spermicides, or the like, through a membrane and into the vaginal area with the added advantages that the unique construction and shape of the present devices allow them to be worn comfortably in the vagina for periods of several weeks and to remain substantially undisturbed within the vaginal cavity during sexual intercourse.

For devices to open after insertion and be retained over the cervical os, they need to be stiff enough to maintain their general shape during wear. The necessary stiffness may be provided by incorporating a rim or bead into the devices. While this allows a device to be positioned and retained well, a rim can undesirably cause awareness of the device during wear and during intercourse.

On the other hand, a device that is soft and compliant conforms well to the vagina and also results in minimal awareness during wear or during intercourse. However, if such devices are too soft or compliant, they will not open to cover the cervix in use.

The construction of the present devices allows them to be positioned in the vagina in such a way that maximum contraceptive protection is secured. As can be seen by reference to the Figures herein, the highly preferred devices of the present type for use within the vaginal cavity are characterized by a comfortable construction and comprise one or more containers, having walls which allow passage of spermicidal surfactant monomers from within the containers into the vagina. The configuration of the devices allows them to be placed in the closest possible proximity to the cervical os, and this feature contributes importantly to their contraceptive efficacy. Indeed, the highly preferred devices herein substantially surround and "cap" the cervical os.

By the present invention, comfortable devices which open after insertion into the vagina are manufactured by incorporating reinforcing means across the back and/or front of the device. The resulting devices open after insertion, conform well to the vagina, and result in minimal awareness during wear or during intercourse.

The reinforcements can be arranged to provide the additional advantage of ensuring that spermicide solution in the device has a pathway to that generally central portion of the device which lies over the cervix. When a device is worn, it may sometimes be flattened by the cervix and the walls of the vagina. If the face of the device which is toward the cervix is pressed against the back of the device, access of surfactant solution to the semi-permeable membrane is blocked. The reinforcements can be arranged to provide internal channels so that even if the membrane of the front face is pressed against the reinforcements on the back, the surfactant solution still has a pathway to that portion of the membrane covering the cervix.

The devices can also be designed in such a way as to provide lobes and/or grooves on the exterior of the device, and, if desired, a plurality of compartments within the device. A lobed or grooved exterior configuration has the advantage of providing external channels along the exterior surface, through which the menses and other biological fluids can pass. It can be appreciated that, since the preferred devices of this invention are designed to cap the cervix, they could potentially allow accumulation of menstrual fluid, cervical mucus, or similar physiological fluids, between the cervix and the device, causing undesirable (although temporary) dilution of the surfactant, inconvenience in removal, and, rarely, problems with odor or infection. However, the between-lobe channels prevent these problems from arising, since the menses are able to flow around the device, rather than accumulating.

A plurality of containers insures that the prolonged, controlled-release characteristics of the device are retained even in the event of rupture, leakage or perforation of some containers during manufacture, handling, or use.

The front and back walls of the present devices comprise polymeric membranes. By using membranes of different thickness, the major part of the contraceptive surfactant agent released from the devices can be directed through the face to the primary situs of contraceptive activity, i.e., to the cervical os, and losses of contraceptive agent by dissipation into the general vaginal area through the back are thereby minimized.

In use, the devices are folded for insertion into the vagina posterior to the introitus such that they are positioned in the closest possible proximity to the cervical os. The reinforcements in the devices cause them to open from the folded position to substantially block or cap the os.

BRIEF DESCRIPTION OF THE DRAWINGS

FIGS. 1, 2 and 3 depict a lobed device of the present invention.

DESCRIPTION OF THE DRAWINGS

Figure 4:
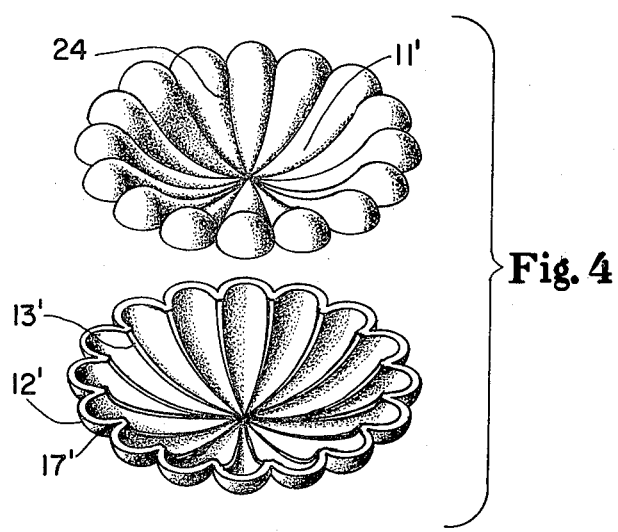
FIGS. 4, 5 and 6 depict a device which is lobed and which further has a plurality of individual compartments.

FIG. 1 is an exploded perspective view of a preferred lobed device of the present type. The device comprises two dish-shaped discs which are assembled into a structure which provides a container for the spermicidal ingredient.

In the device of FIG. 1, the front face 11 comprises a membrane which is permeable to surfactant monomers but which is not permeable to the passage of surfactant micelles therethrough. The front face 11 is formed with regular, approximately hemispherical lobes 16 along the periphery, projecting convexly from the overall concavity which the front face presents to the cervical os.

The back half 12 of the preferred device comprises a flexible, toxicologically-acceptable material which is formed with flexible reinforcing ribs 13 on the inner surface and corresponding grooves 17 on the outer surface, providing a scalloped peripheral contour, matching the lobes 16 formed in the front face. The toxicologically-acceptable material used to fashion this outer portion of the device is not critical and need not be a semi-permeable membrane material.

FIG. 1 depicts the front face 11 and back 12 of the device in proper juxtaposition for assembly. To assemble the device, the edges can be sealed in any suitable fashion such as polymer welding or adhesive sealing, thereby leading to the assembled device depicted in perspective view as FIG. 2.

FIG. 3 is a section view of the assembled device through line 3—3 of FIG. 2, showing the relationship of the front face 11, which constitutes the transport surface for the spermicide, the back 12, and sealed edges 14.

The device of FIG. 3 comprising a container formed by joining the two halves of the device is depicted as being substantially filled with an aqueous solution of spermicidal surfactant 15.

The device of FIG. 3 is depicted with the back wall 12 being somewhat thicker overall than the front face 11. This connotes, in the preferred device herein, a back wall which is less permeable to transport of surfactant than the front face. This difference in permeability serves to direct surfactant monomers preferentially through membrane 11, which is placed in proximity to the cervical os.

In use, the device herein is folded for insertion into the vagina posterior to the introitus. Once inserted, the reinforcing ribs cause the device to open and to substantially block or cap the cervical os such that semi-permeable membrane 11 is in the closest possible proximity to the os. Placement of the semi-permeable membrane adjacent to the cervical os causes the os to be bathed in the spermicidal surfactant as monomers thereof are released through the surfactant transport surface which comprises membrane 11. The indentations or grooves formed between lobes of the lobed devices allow the menses to flow out around the device at the end of the wear period. Sperm which pass through the grooves are rapidly killed by surfactant released through membrane 11.

After insertion, the position of the device of FIGS. 1-3 can be checked digitally. If the device has been inserted backwards, that is, so that the front face 11 faces away from the cervical os, the smooth transport surface will be felt, rather than the grooved back. The device can then be removed and reinserted in the proper position to provide maximum contraceptive protection. However, since these devices are worn for long periods, typically a month, repeated removals and reinsertions are not necessary.

FIG. 4 is an exploded perspective view of a lobed device similar to that in FIGS. 1-3, but in wich reinforcing ribs (not shown) and corresponding grooves 17' are formed in the front face 11', to oppose those in the back, 12' and 17', respectively. When the two halves of the device are assembled by any suitable technique, including polymer welding or adhesive sealing, the matching reinforcements in the respective halves also abut and are sealed together, forming a device having a plurality of "teardrop"-shaped compartments 18, as shown in perspective in FIG. 5.

Figure 5:
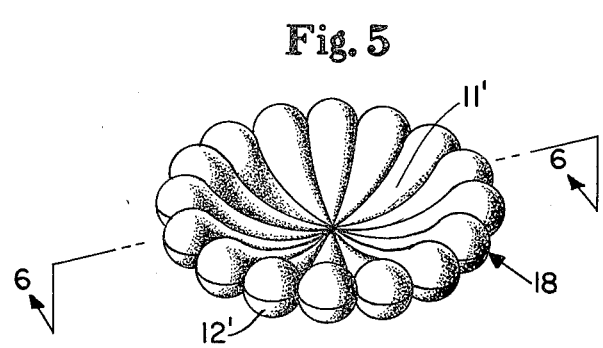
Figure 6:
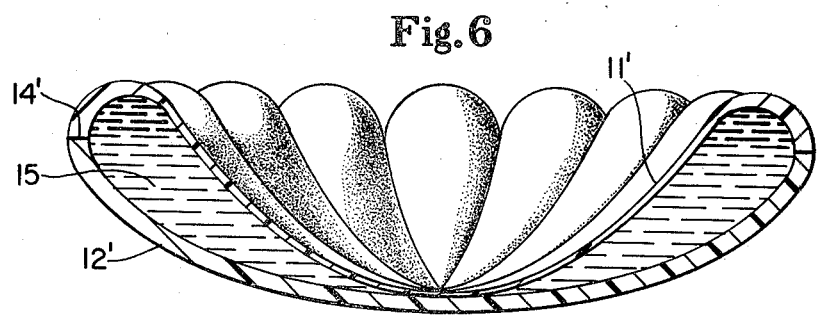

FIG. 6 is a section view of the assembled device through line 6—6 of FIG. 5, which bisects two of the compartments. FIG. 6 illustrates the relationship of the front face 11', which constitutes the transport surface for the spermicide 15, the back 12', and the sealed edges 14'.

In addition to having the advantages provided by the lobed device, the device of FIGS. 4-6 provides continuous spermicidal protection even if some of the compartments leak or are perforated or rupture during manufacture, handling, or use. Thus, the device of FIGS. 4-6 is especially preferred.

Figure 7:
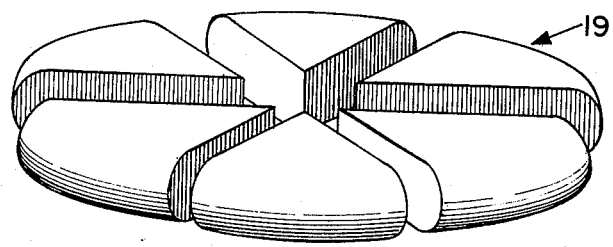
FIGS. 7, 8 and 9 depict a non-lobed device formed with a plurality of compartments.

FIG. 7 is an exploded perspective view of a device assembled so that the container is partitioned into a plurality of compartments by the incorporated reinforcements. The individual "pie-shaped" segments 19 can be assembled from individual halves, as are the devices of FIGS. 1-6, or they can be formed as units by techniques such as blow-molding. In either process, the finished device, assembled from the segments as shown in FIG. 8, is differentiable into the front face 20 and back 21, the front face providing a semipermeable membrane transport surface, which in use is placed in close proximity to the cervical os.

Figure 8:
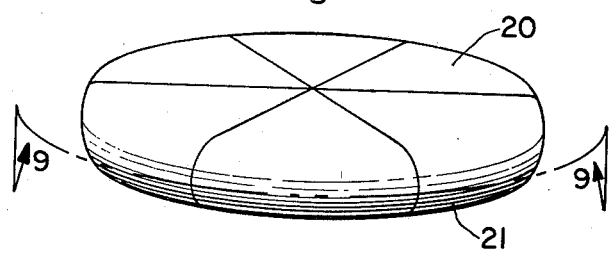
Figure 9:
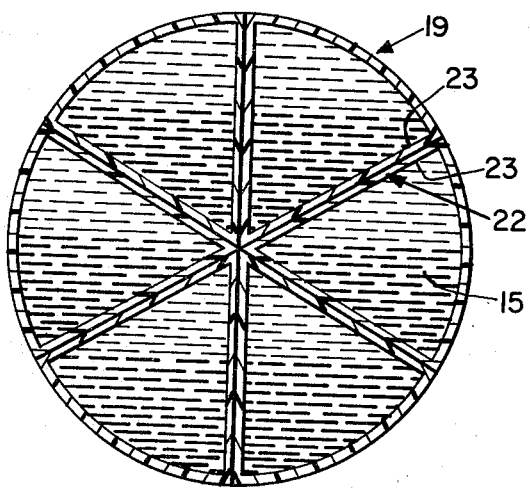

FIG. 9 is a section view of the assembled device through line 9—9 of FIG. 8, showing the relationship of the individual segments 19 when assembled by techniques such as polymer welding or adhesive sealing into a finished container partitioned by the reinforcements 22, formed by juxtaposition and joinder of individual segment sidewalls 23. FIG. 9 shows each compartment as containing an aqueous solution of a spermicidal surfactant 15.

The device of FIGS. 7-9, being discoid in shape, is folded for easy insertion and is placed in the vagina, posterior to the introitus and in close proximity to the cervical os, where the rigidity imparted by the inner reinforcements 22 causes the device to unfold and substantially block the cervical os, while spermicidal surfactant diffuses from the transport surface of the front face and bathes the cervical os, thereby assuring contraceptive efficacy in the event sperm are deposited behind the device.

DISCLOSURE OF THE INVENTION

The contraceptive devices of this invention make use of the association colloid nature of solutions of certain spermicidal surfactants to provide a reservoir from which spermicide is released in a controlled manner through the semi-permeable membrane which comprises at least a portion of the wall of the device. Surfactant micelles, as is, cannot diffuse through the semipermeable membrane; they must first dissociate, at or remote from the membrane, to individual surfactant molecules which then dissolve in the membrane material and diffuse therethrough to its outer surface, whereupon the surfactant monomers are free to dissolve in the surrounding vaginal fluid to provide their contraceptive effect. Since the predominant driving force for diffusion is the concentration different between unassociated (i.e., monomeric) surfactant molecules in the solution inside and outside the contraceptive device, the rate of transport will slow drastically when the exterior surfactant monomer concentration approaches that on the interior of the device, thus producing a desirable controlled release of the surfactant through the membrane. In the present devices, the bulk of the surfactant remains in micellar form, where it resides in reserve within the device to provide a source of monomers over a long period of time, thereby delivering continuous contraceptive protection to the user for a time period of 20-30 days, or more.

As will be seen from the following disclosure, the present invention encompasses contraceptive devices which are especially adapted for use within the vaginal cavity at a position posterior to the introitus and in close proximity to the cervical os, comprising: a circumferentially lobed, dish-shaped container, said container being formed from: a dish-shaped, scalloped back, said back being characterized by one or more thickened, reinforced areas, and a circumferentially lobed front face capping said back, at least a portion of said front face being a non-porous semi-permeable membrane transport surface; said container being substantially filled with an aqueous solution of a micelle-forming spermicidal surfactant compound at a concentration greater than or equal to the critical micelle concentration of said surfactant compound. Preferred devices are those wherein the transport surface extends substantially across the face of the device. Dish-shaped, scalloped or lobed devices which can be positioned to substantially block or cap the cervical os are an especially preferred embodiment of the invention.

The present invention also provides a contraceptive device especially adapted for use within the vaginal cavity, comprising a dish-shaped or disc-shaped container, said container being characterized by one or more internal reinforcing walls, said container being partitioned by said reinforcing walls into a plurality of compartments, said compartments containing an aqueous solution of a micelle-forming surfactant compound at a concentration greater than or equal to the critical micelle concentration of said surfactant compound, a portion of an external surface of said container being a non-porous, semi-permeable membrane transport surface.

Devices according to this invention wherein only the container walls which face the cervical os comprise the substantially non-porous, semi-permeable membrane transport surface in the device are preferred for use as contraceptives, inasmuch as the spermicidal surfactant is thereby delivered directly to its prime situs of action. Moreover, delivery of excess surfactant to the general vaginal cavity is thereby avoided. However, devices wherein all container walls comprise the substantially non-porous, semi-permeable membrane transport surface are also useful and are encompassed by this invention.

The most highly preferred embodiment of the present contraceptive devices comprises: a circumferentially lobed, dish-shaped container formed from a dish-shaped, scalloped, reinforced back, and a circumferentially lobed front face capping the back, substantially the entire front face being a non-porous semi-permeable membrane transport surface having a thickness in the range of from about 0.1 mm to about 0.6 mm, said container holding an aqueous solution of from 10% to about 50% by weight of $C_{10}EO_5$ and/or $C_{10}EO_6$. Such devices wherein the container is partitioned by the reinforcements into a plurality of closed compartments, and especially those devices wherein only the wall facing the cervical os comprises the semi-permeable membrane (transport surface), are especially useful and preferred herein.

This invention also provides a method for achieving contraception, comprising: inserting within the vaginal cavity at position posterior to the introitus and in close proximity to the cervical os a device of the present invention, and placing the device so that the transport surface substantially caps or blocks the cervical os, whereby surfactant monomers diffuse from the device and substantially bathe the cervical os to provide a spermicidal effect.

The devices herein are prepared from components which are described in detail hereinafter.

The configuration of the devices herein is designed to provide a semi-permeable membrane as a transport surface for the surfactant monomers, said transport surface extending across the entire surface of the cervix (i.e., substantially covering the cervical os). This eliminates problems occasioned by small lateral movements of the device associated with muscular contractions/exertions of the user during wear. Most importantly, by providing a transport surface which is in the closest possible proximity to the cervix, the surfactant has the shortest possible path to the cervical os. Since conception is associated with transmittal of sperm into the os, it will be appreciated that, by delivering surfactant monomers in the most efficient manner to this point in the vagina, the most efficient and effective contraceptive protection is provided.

BACKGROUND ART

The configuration of the present devices allows them to be positioned in close proximity to the cervical os (i.e., actually touching or within a distance of ca. 1 mm to 10 mm), and substantially overlying and capping the cervical os. Thus, the present devices deliver the spermicidal surfactants more efficiently and effectively than the devices disclosed in the Gougeon and Drobish U.S. Pat. Nos. 3,991,760 (Nov. 16, 1976); 3,995,633 (Dec. 7, 1976) and 3,995,634 (Dec. 7, 1976).

The reinforcements and, preferably, lobes used in the present devices allow them to be fashioned in a foldable, yet vaginally-retainable design which is substantially more comfortable in use than the rimmed devices disclosed by Drobish and Gougeon in U.S. Application Ser. No. 748,267, filed Dec. 7, 1976.

Controlled release devices of the present type respond rapidly to changes such as dilution effects in the external environment, e.g., by body fluid changes, whereas some sustained release articles do not; see Cowsar, in "Advances in Experimental Medicine and Biology", Vol. 49, "Controlled Release of Biologically Active Agents", Ed. Tanquary and Lacey, Plenum Press, New York 1974. The net result is that the present devices are capable of rapidly establishing an effective level or concentration of a medicament or other agent in a selected environment, and then maintaining the concentration at that level. In contrast, many sustained release articles dispense an agent at a constant rate and often do not display the feedback regulation of release that a controlled release article displays.

It will be appreciated that devices operating by the controlled release mechanism provide substantial advantages over sustained release articles for certain uses. For example, placement of a properly formulated controlled release medicament system in an animal's body cavity in contact with body fluids establishes and maintains an effective concentration of the medicament in the fluids. The system responds to dilution or depletion as additional fluids are secreted, or the medicament is bound to tissue, absorbed, etc., thereby automatically maintaining the concentration of medicament at the proper level.

As disclosed by Laughlin in German No. 2,610,880, open to inspection Oct. 7, 1976, solutions of micelle-forming surfactant compounds can be releasably enclosed in a container comprising a microporous membrane. Articles thus prepared are stable and do not suffer osmotic rupture when placed in the body cavities in contact with body fluids. Rather, the stable articles provide controlled release of the surfactant into the bosdy fluids. The proper selection of membrane and surfactant provides a means for achieving various biological effects, e.g., antimicrobial activity, spermicidal activity, and the like. Laughlin teaches the use of porous membranes such as cellulose. However, cellulose is fragile and is quite difficult to fashion into controlled release devices.

In the present invention various non-porous elastomers are fashioned into membranes which allow passage of spermicidal surfactant monomers therethrough a controlled manner. Such membranes are not fragile; accordingly, stable controlled release articles with optimal shapes for providing vaginal contraceptive protection are readily made therefrom.

Moreover, the membranes used in the present devices are substantially impervious to liquid water. In use, the monomers of spermicidal surfactant diffuse through the membrane into the vagina (presumably by virtue of their solubility in the membrane), whereas the surfactant micelles do not. Since the membranes are non-porous and are substantially impervious to bulk water and body fluids, they do not undesirably develop an internal pressure in an aqueous environment.

In contrast, osmotic pressure causes some rigidity in the devices of Laughlin, which can aid in their retention in the vagina. However, development of internal hydrostatic pressure due to osmotic effects can cause at least two disadvantages in the Laughlin devices: (1) this pressure stresses the membrane structural components of the device making them more prone to rupture under the influence of external force than they would be otherwise; and (2) this pressure precludes the use of products having relatively broad unsupported membrane areas as provided in the present vaginal contraceptive application. Products so designed would undesirably inflate to uncomfortable and potentially contraceptively ineffective shapes. In any case, osmotic pressure is not, per se, the force which moves surfactant out of either the Laughlin devices or the devices disclosed herein. Rather, in both cases, it is the transmembrane chemical potential (i.e., substantially the surfactant monomer concentration) difference which causes release of spermicidal surfactant monomers from the device. However, as noted above, Laughlin employs microporous membranes, such as swollen cellulose, which comprise microporous, water-filled channels through which the monomers are transported. In contrast, the present devices use non-porous membrane materials through which the surfactant monomers migrate by first dissolving therein then diffusing therethrough.

Moreover, the devices herein do not operate by an osmotic pressure mechanism and are thus entirely different from that of art-disclosed, osmotically-actuated "pump" devices for delivering drugs.

Highly preferred devices are those operating by a controlled release mechanism. However, devices operating by a sustained release mechanism can also be constructed in the manner disclosed herein so that they can be retained in the vagina during intercourse. Accordingly, sustained release devices of the unique construction and shape of the devices herein are fully contemplated by this invention.

BEST MODE

Container

Broadly, the present devices comprise a container, having a single or multiple compartments, said container being insoluble in vaginal fluids, in a total device of the configuration described herein. The container has the surfactant solution enclosed therein. At least one portion of the container comprises a non-porous polymeric semi-permeable membrane which permits the release of surfactant monomers into the vagina, but which substantially prevents the transport of the larger surfactant micelles. In short, the membrane is the transport surface which selectively discriminates between passage of monomers and micelles.

Containers used in the present devices can be partly made of any stable material such as glass, plastic, etc., which is not permeable, even to surfactant monomers. Of course, the containers should be made from a material which is inert to the surfactant solutions being used, as well as to the vaginal tissues, but selection of inert container materials is not a problem. At least some portion of the container used in the present devices must comprise a non-microporous polymeric semi-permeable membrane which allows diffusion of the spermicidal surfactant monomers therethrough and into the vaginal cavity. For the reasons disclosed above, at least that wall of the container which faces the cervical os comprises the controlled release membrane. Alternatively, the entire device can be made of the membrane material.

Preferred controlled release devices are those wherein the container wall is a dish-shaped or disc-shaped envelope, one face of which is the controlled release membrane.

An especially preferred embodiment of this invention is a circumferentially lobed, dish-shaped silicone polymer container, said container being formed from: a thin, flexible, comfortable back having a scalloped periphery, the concave surface of the back being characterized by one or more radially distributed thickened, reinforced areas corresponding to the scalloped periphery and a circumferentially lobed front face capping the back, the lobes in the front face being shaped to meet the scalloped periphery of the back when the front face and back are joined, a portion of the front face being a non-porous, semi-permeable membrane transport surface; said container being substantially filled with an aqueous solution of $C_{10}EO_5$, $C_{10}EO_6$, or mixture thereof.

The semi-permeable membranes used in the controlled release devices are characterized by parameters which reflect their strength, integrity and ability to pass surfactant monomers and to retain surfactant micelles, as follows.

The membranes should be substantially water-insoluble so that they maintain their strength and integrity when in contact with body fluids.

Since the devices are to be used in contact with body fluids and tissues, the membranes (and total container and device) should be toxicologically acceptable. Moreover, the membrane material will most preferably be immunologically acceptable and will not be rejected by the body's natural defense mechanisms nor have any untoward effect on the rate of antibody formation, and the like.

The membrane must possess the ability to provide metered release of the surfactant monomers in order to provide the prolonged contraceptive benefit of the article.

The membrane must be sufficiently strong and made of a material that can be fashioned into the highly preferred shapes of the devices disclosed herein.

The semi-permeable membranes employed herein comprise non-porous elastomers, preferably silicone polymers or latex rubbers, either natural or synthetic. The membranes generally have a thickness in the range from about 0.02 mm to about 0.6 mm, preferably about 0.1 mm to about 0.4 mm. By selecting a membrane thickness within this range, stable, non-fragile, yet flexible and comfortable articles which effectively transport surfactant monomers to the vagina are provided.

The silicone polymers used in preparing the membranes for use in the present devices are preferably polydimethylsiloxanes, i.e., silicone polymers which contain the repeating unit

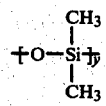

wherein y is an integer in the range of about 100–100,000.

Repeating units of the silicone polymer can contain side-chain branching and cross-linking, e.g.,

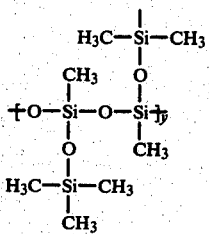

Various functional groups may be present in the basic silicone polymer structure to facilitate cross-linking/curing.

Silicone polymers suitable for use herein can be prepared, for example, by hydrolyzing dimethyldichlorosilane or mixtures of dimethyldichlorosilane, trichloromethylsilane and chlorotrimethylsilane with water, in well-known fashion. Alternatively, siloxane "oligomers" can be polymerized and "cured" in various ways well known in the art. Silicone polymers suitable for preparing the membranes for use in the present invention are also available, commercially, from suppliers such as the Dow Corning Corporation and the General Electric Corporation.

The latex rubbers which can be used in the present invention can be either the natural or synthetic latex rubber polymers which are commercially available. Such materials include, for example, the neoprene-type rubbers, the Buna ®-type rubbers, and the like. Natural or synthetic rubber which is calendered or molded can also be used.

Other types of non-porous polymers which can be used to fashion membranes for use with devices of the present type comprise, for example, mixtures of silicone polymers and latex rubbers; copolymers of silicone polymers and various other polymeric materials such as the polycarbonates, and the like; elastomers such as the well-known styrene/butadiene block copolymers; ethylene-vinyl acetate copolymers, etc.

Various polymeric membranes suitable for use in the contraceptive devices of the present invention can be determined easily using the Surfactant Transport Procedure, disclosed hereinafter.

Highly preferred membranes for use herein are the non-porous membranes comprising silicone polymers, especially the polydimethylsiloxanes manufactured under "clean" conditions and marketed for various medical uses. Such materials are safe for prolonged use in contact with human tissues and provide excellent transport of surfactant monomers, especially the preferred, nonionic spermicidal surfactants of the type $C_{10}EO_5$ and $C_{10}EO_6$, as described hereinafter. These silicone polymers can readily be fashioned into membranes for use in devices having the preferred configurations disclosed herein. Typical examples of such silicone materials include Silastic ® 382 and Dow Corning ® MDX 4-4210, MDX 4-4515, MDX 4-4516, Q7-2213, Q7-2245, and X7-2177 available from the Dow Corning Corporation.

SPERMICIDAL SURFACTANT

The use of micelle-forming surfactant solutions in the present contraceptive devices results in several important advantages over other types of metered dosage systems.

First, the surfactants employed as the active agent of the contraceptive devices of the present invention appear to function by an entirely localized effect on motile sperm. (The terms "spermicide" and "spermicidal" as employed herein encompass surfactants which truly "kill" animal, including human, sperm as well as those which immobilize or otherwise render sperm cells inactive.) Accordingly, undesirable side-effects which can accompany the prolonged use of systemic contraceptive drugs such as hormones are avoided.

Moreover, the use of safe, effective surfactants as the spermicide permits the formulator of the present devices to employ a large excess of the spermicide therewith. The controlled release feature allows formulation of devices containing more spermicide (surfactant) than the usual expected need for an extended wear period, but (1) reduces the probability of side-effects by regulating the concentration produced in the vaginal fluids to a minimum level, and (2) allows for unusual variations in the amount of spermicide required or in the time period over which it might be needed. Accordingly, a "safety factor" of the order of several-fold vis-a-vis prolonged contraceptive efficacy is provided by the present devices.

The devices herein can be somewhat flaccid, rather than turgid. Accordingly, the pressure differential across the enclosing container is small, or zero, and the container is stable and is not subject to hydrostatic rupture. This desirable attribute of the present devices is to be contrasted with the situation which occurs when a similarly concentrated solution of a non-micelle-forming solute of similar molecular weight is enclosed by a water-permeable diffusion membrane, whereupon internal hydrostatic pressures of tens or hundreds of atmospheres can be developed due to osmotic effects, thereby leading to rupture of the membrane.

The surfactants employed in the present devices and processes are characterized by several parameters. In general, the surfactants are selected from those which, in combination with the semi-permeable membrane described hereinabove, provide an appropriate relationship between release and the desired contraceptive end use of the devices.

The surfactants herein are characterized by their ability to dissolve in a solvent (normally, water) and to form an association colloid, or micelles, therein. It has now been discovered that the surfactant micelles do not penetrate the walls of the membranous containers used herein. However, surfactant monomers do diffuse through the membranous walls and into the vagina. Thus, by virtue of the equilibrium between micellar and monomeric surfactant, the solution of surfactant micelles provides a reservoir for the controlled delivery of spermicidal surfactant monomers to the environment external to the device, i.e., the vagina, especially the area immediately around the cervical os. In a surfactant solution which is sufficiently concentrated to form true micelles, the concentration of monomer in equilibrium with the micellar surfactant remains substantially constant at the so-called "critical micelle concentration" (cmc) over a wide range of total surfactant concentration. In order to realize fully the unique advantages of surfactants in devices of the present type, it is preferred to use those spermicidal surfactants having a cmc of at most about $5 \times 10^{-3}$ Molar (M). In particular, by choosing surfactants with this low cmc, the user of the present devices is exposed to only minimum amounts of surfactant, thereby minimizing any possible toxicological hazards.

It is to be appreciated that "neat" surfactants, i.e., surfactants not in solution, are not in the form of micellar aggregates and, accordingly, simply pass through the walls of the membranes in an undesirable, uncontrolled manner, thereby eliminating the reservoir effect provided by surfactant micelles.

When used as between-period contraceptives, it is, of course, necessary to select surfactants which produce the desired spermicidal response. Moreover, to secure the benefits of controlled release, it is necessary also to select surfactants whose monomers are rapidly transported through the membranous walls of the container to establish an effective concentration of surfactant in the vaginal area.

From the foregoing considerations it will be appreciated that various surfactants can be tested in vitro in a simple medium which approximates various body fluids (such as physiological saline or distilled water) to determine the concentration at which the surfactant must be present in such medium to provide spermicidal efficacy. Surfactants whose monomers are transported through the enclosing membrane of the device to provide at least the aforesaid effective concentration in the medium are useful herein. Upon immersion in an external solvent (e.g., vaginal fluids) the controlled release devices herein deliver surfactant monomers to the external solvent in the rapid, or "primary", transport process. After this external concentration reaches, approximately, the cmc of the surfactant, monomer transport slows drastically, since monomer concentration on both sides of the semi-permeable membrane is nearly equal. Slower, "secondary" transport processes may carry a bit more of the surfactant through the membrane to the vagina, but this does not substantially deplete the surfactant reservoir in the present devices.

From the foregoing, it follows that, for the desired spermicidal effect to be realized, the ratio, R, of the cmc of the surfactant to its spermicidally-effective concentration, $C_{sperm.}$, e.g., in saline, i.e., $$R = cmc/C_{sperm}$$

should be greater than or equal to about 1. Similar considerations hold for external media other than saline, i.e., fluid media such as vaginal fluids, water, etc., in which the present surfactant monomers are soluble. Accordingly, the preferred compounds for use in the devices described herein have values of R which are greater than or equal to ca. 1, i.e., $$R \geq ca. 1.$$

A variety of surfactants exhibit a cmc less than about $5 \times 10^{-3}$ M and meet this criteria for use in the preferred controlled release devices herein. Several surfactant types having this preferred cmc provide a desirable spermicidal response. Moreover, several surfactants exhibit the requisite relationship, $R \geq ca. 1$, between cmc and spermicidal activity.

Based solely on the foregoing considerations, representative examples of surfactants useful herein include nonionic surfactants such as n-$C_{10}H_{21}(OCH_2CH_2)_5OH$ (abb. $C_{10}EO_5$) and n-$C_{10}H_{21}(OCH_2CH_2)_6OH$ ($C_{10}EO_6$); semipolar surfactants such as $C_{12}H_{25}S(NH)_2CH_3$ and $C_{12}H_{25}(CH_3)_2AsO$; and cationic surfactants such as $C_{16}H_{33}N^+(CH_3)c,Cl^-$ and $C_{16}H_{33}N^+C_5H_5,Cl^-$. These surfactants are characterized by $R \geq 2$ and $cmc < 10^{-3}$ M.

It is to be understood that other surfactants having a cmc of about $10^{-3}$ M, or less, but which exhibit somewhat lower activity as spermicidal agents, i.e., surfactants wherein ca. $1 \leq R < 2$, can be employed in controlled release articles. However, the biological response to these latter surfactants is somewhat less than that of the preferred group, and the efficacy margin, i.e., R-1, is not as great. Included among this group of surfactants are n-$C_{12}EO_9$; n-$C_{16}EO_1SO_4^-$, $NA^+$; $C_{12}H_{25}(CH_3)_2PO$; n-$C_{10}EO_4$; $C_{12}H_{25}(C_2H_5)_2PO$; $C_{16}H_{33}$ ammoniopropanesulfonate; and nonylphenol nonaethoxylate.

As can be seen from the foregoing, various surfactant types are useful in controlled release contraceptive devices of the present type. However, when devices designed for use as between-period contraceptives in humans are being prepared, additional physio-chemical properties of the surfactants must be considered. For example, the surfactants should be toxicologically acceptable for use in the body over extended time periods. The surfactants should also be non-irritating to the delicate tissues of the vagina and uterus. The preferred surfactants should not excessively bind serum proteins found in the vaginal area between periods of menstrual flow, inasmuch as the bound surfactant-protein moiety does not function as a spermicide and binding accelerates the depletion of surfactant from the reservoir (micelles) within the device. The surfactant monomers must be able to dissolve or partition into the enclosing membrane of the device and diffuse through the membrane in an efficient and effective manner. Finally, the surfactant should be selected from those which do not bind to charged sites in the enclosing diffusion membrane, since binding inhibits the passage of the surfactant monomers through the membrane. In particular, ionic surfactants are troublesome in this regard. Moreover, some ionic surfactants are too polar to partition into or diffuse through the preferred silicone membranes efficiently.

Based on the foregoing factors, and considering the high spermicidal activity of the compounds, the alkylene oxide nonionic surfactants, especially the well-known condensation products of ethylene oxide with aliphatic alcohols or alkyl phenols, are preferred for use herein. In particular, $C_{10}EO_5$ and $C_{10}EO_6$ surfactants are most preferred for use in the present controlled release contraceptive devices. As between these latter compounds, $C_{10}EO_5$ has the advantage of the lower molecular weight, and therefore provides more spermicidal monomer per given weight of compound. Accordingly, $C_{10}EO_5$ is most preferred for use in the between-period, controlled release contraceptive devices of this invention.

The surfactants disclosed hereinabove are all well known from the detergency arts and can be made by various art-disclosed processes.

SURFACTANT TRANSPORT PROCEDURE

A cell for testing transport of surfactant monomers through membranes is as follows. A 40 mm (diameter)×50 mm (length) poly-methylmethacrylate rod is halved and each half is suitably machined to provide cavities 16 mm (diameter)×10 mm (depth), such that the cavities abut when the rod halves are reassembled. Each cavity is provided with two inlet holes for filling and sampling. A brass clamp is used to hold the two cell halves firmly together.

The surfactant transport testing is carried out in the following manner. A disc 3 cm in diameter of the membrane material to be tested is sandwiched between the cell halves, enclosing a 3 mm glass bead on each side of the membrane to provide stirring. One half of the cell is filled with distilled water and the other half is filled with an aqueous solution of a radiolabeled surfactant. The inlet holes are sealed with waterproof tape and the cell is placed in a 37° C. bath in a device which allows the cell to be rotated axially at approximately 50 rpm. Periodically, the cell is raised from the bath and the solution in the desired compartment sampled.

A typical procedure using a membrane of polydimethylsiloxane (Dow Corning® MDX 4-4210) is as follows. After charging the cell, the cell is maintained in the 37° C. bath for varying time periods, after each of which the tape is removed from the inlet holes and duplicate 10 microliter (µl) samples are removed by syringe and expressed into a counting vial. In the subsequent scintillation counting, each sample vial is charged with 10 milliliters (ml) of a solution of 0.8% 2-diphenyloxazole and 0.01% of 1,4-bis-[2-(4-methyl-5-phenyloxazolyl)]-benzene in a 1:1 ethanol/toluene mixture. The vials (two for each time period) are then placed in the refrigerator compartment of a counting instrument and cooled to 4° C. before being counted for 5 minutes each. The counts per minute are converted to ppm by applying a factor found by counting one or more standard samples. By taking samples at regular intervals, a curve plotting the surfactant concentration in the initially surfactant-free side of the cell versus the time of sampling can be drawn which describes the transport of the surfactant across the membrane.

Following the Surfactant Transport Procedure set forth hereinabove, the cell cavity designated (A) is charged with surfactant solution and the cavity designated (B) is charged with distilled water. The cell cavities are separated by the test membrane, e.g., polydimethylsiloxane. The concentration of surfactant transported to cavity (B) is determined in the foregoing manner, and the graph of the concentration of surfactant in (B) versus time is plotted.

This graph describes a monomer transport curve which at the outset rises at a high rate (primary slope) and beyond a certain time rises at a much lower rate (secondary slope). The monomer transport curve has the general form $C=C_2(1-e^{t/\tau})+S_2 t$, where $C=$surfactant concentration in cavity (B), $C_2=$the zero time intercept of the secondary slope, $t=$time, $\tau=$the time constant, and $S_2=$the secondary slope. The primary slope, $S_1$, is the slope of the curve at $t=0$ and is given by $$S_1 = (C_2/\tau) + S_2.$$

For controlled release devices of the present type, the combination of surfactant and a suitable membrane should yield a monomer transport curve wherein $S_1$ is relatively large, $S_2$ is relatively small, and $C_2$ is about equal to the cmc of the surfactant being tested. The ratio of $S_2/S_1$ is from 0 to about 0.1. $S_1$ should generally be no less than about 10 ppm/hr. and preferably will be in the range of about 100 ppm/hr. to about 200 ppm/hr.

Based on the foregoing, surfactant/membrane combinations can be selected which will provide controlled release articles of the present type. A highly preferred article herein which is particularly useful as a vaginal contraceptive comprises from about a 5% to about a 50% (wt.) aqueous solution of $C_{10}EO_5$ enclosed within a polydimethylsiloxane membrane.

METHOD OF MANUFACTURE

The following describes a typical method of manufacturing a device of the type depicted in the Figures herein (or the "segments" of the device of FIGS. 7–9). While the description relates to a preferred and convenient process for preparing such devices from a silicone polymer, various methods of manufacture can be employed to prepare other devices encompassed by the present invention.

Dow Corning® MDX 4-4210 Clean Grade Elastomer (Dow Corning Corporation, Midland, Mich.) is supplied in two parts: an elastomer base and a curing agent which, when mixed and cured, form the finished silicone polymer membrane transport surface 11. In practice, about 10 parts of elastomer base are mixed with about 1 part of curing agent. The mixture is deaerated in a vacuum chamber until no more entrapped air can be seen. The deaerated mixture is then injected into a mold cavity of appropriate dimensions for silicone membrane. The silicone membrane is cured by heating in the mold at ca. 125° C. for at least about 15 minutes. It will be appreciated that the mold dimensions can be adjusted to provide the desired thickness of the resulting silicone membrane.

The choice of curing agent for silicone polymers is not critical to the operation of the devices prepared in the manner of this invention. Depending on the particular silicone polymer chosen, various platinum-based, tin-based and peroxide-based catalysts or curing agents for silicones well known in the art are suitable for use in preparing silicone membranes. However, it has now been discovered that, in prolonged use in the vagina, some curing agents can cause the silicone membrane to become discolored. While this discoloration does not deleteriously affect the operation of the devices, they are rendered unsanitary in appearance. Apparently, some naturally-occurring sulfur and/or amino compounds present in vaginal fluids somehow interact with tin-based curing agents such as stannous octoate to cause the discoloration. Whatever the cause, it is preferable, from an aesthetic standpoint, to avoid the use of tin-based curing agents and curing agents which form colored complexes with the components of vaginal fluids in the preparation of optimized articles of the present type. Accordingly, peroxide-based or, preferably, platinum-based silicone curing agents are preferred for use herein. Such materials are well known in the art and can be selected from listings in standard texts. Alternatively, suitable polymers substantially free from color-forming curing agents can be selected by preparing and curing silicone polymers in standard fashion and incubating the polymers in the vaginas of live laboratory animals to determine their propensity for discoloration.

The other half (12) of the device is molded from a polymer (e.g., from silicone) in a die which is machined to provide the desired reinforced shape.

After having prepared the two halves of the device, a uniform layer of silicone adhesive (e.g., Silastic ® Medical Adhesive Silicone Type A, Dow Corning Corporation) is placed along the opposing edges of the upper half (11) and the lower half (12) of the device. The upper half (11) and lower half (12) are joined and pressed to squeeze out any excess adhesive from the seal areas. The excess adhesive is removed from the exterior of the device and the adhesive which seals the device is allowed to cure for 24 hours, or longer.

An aqueous solution of the spermicidal surfactant is prepared. The solution is taken up in a syringe fitted with a 25 gauge needle. The surfactant solution is injected into the free space or spaces within the device. With the needle still in place, any air remaining inside the device is removed. (Needle holes from this procedure do not leak with pressures encountered in use.)

In an alternative filling procedure, one half of the device is positioned as shown in the Figures, the surfactant solution is poured into this half, and the other half of the device is sealed thereto with the surfactant solution in place in such a way as to avoid entrapping any air within the device. Alternatively, any entrapped air can be removed with a needle and syringe, as above.

After filling, the sealed device is placed in a retortable foil-plastic laminate pouch which is hermetically sealed. The pouch is placed in a retort at 30 psig for 30 minutes. After cooling, the retort is opened and the pouches are removed to provide individually packaged, sterile contraceptive devices suitable for distribution to users.

INDUSTRIAL APPLICABILITY

The following examples illustrate the practice of this invention, but are not intended to be limiting thereof. It is to be understood that the present invention also encompasses devices wherein the front (transport surface) face is reinforced and wherein the back is either reinforced or not, at the option of the manufacturer. Devices of this "reverse" construction are manufactured in the manner and with the materials disclosed herein.

EXAMPLE I

A device of the type depicted in FIG. 2 is prepared from Dow Corning ® MDX 4-4210 Clean Grade Elastomer using the methods described hereinabove. The device is in the form of a lobed dish formed from two separately cast halves comprising the MDX 4-4210 silicone material. The thickness of the front face of the device which comprises the transport surface membrane (11) is ca. $0.35 \pm 0.15$ mm, whereas the thickness of the outer half (12) is ca. $1.00 \pm 0.15$ mm. The thickness of the reinforcing ribs (13) cast into the outer half of the device is ca. 3 mm. The base of the device has an outside diameter of ca. $55 \pm 10$ mm. The distance from the front face lobes to the back of the device is ca. $20 \pm 5$ mm, whereas the distance from the membrane to the back of the device is ca. $15 \pm 5$ mm, whereby the total volume of the dish-shaped container resulting from sealing the edges of the device is ca. 4–6 cc.

A device of the foregoing type is substantially filled with a 25% (wt.) aqueous solution of the $C_{10}EO_5$ surfactant. Excess air is removed. The device is autoclaved and is ready for use as a vaginal contraceptive.

The device is folded in half and placed in the vagina posterior to the introitus in a manner such that the transport surface 11 substantially covers and "caps" the cervical os. The device opens automatically to cap the os, by virtue of the reinforcing ribs. The device is worn during the time between menses and safely and continuously delivers a spermicidally effective amount of $C_{10}EO_5$ surfactant directly to the cervical os. In particular, the positioning and shape of the device bathes the cervical os with the spermicidal surfactant. The device is quite comfortable and remains in place during intercourse.

In the device of Example I, the $C_{10}EO_5$ surfactant is replaced by an equivalent amount of $C_{10}EO_6$ surfactant and excellent spermicidal results are secured.

EXAMPLE II

A device of the configuration depicted in FIG. 5 is prepared as follows. The lobed front face of the device (i.e., the transport surface (11) to be placed in close proximity to the cervical os) is prepared from Dow Corning ® MDX 4-4210 Clean Grade Elastomer using the methods described in Example I. The thickness of the silicone membrane is ca. $0.25 \pm 0.15$ mm.

The other half of the device is prepared from a substantially non-permeable, polyethylene (PE) plastic having a thickness of ca. $0.35 \pm 0.15$ mm. Reinforcing ridges (ca. 3 mm. thickness) and corresponding grooves of the type depicted in FIG. 4 are cast into both halves of the device.

The two halves are assembled in the manner described above to provide a lobed, dish-shaped, multi-compartment device. The concavity of the front face comprises the semi-permeable silicone membrane. The base of the device has an outside diameter of ca. $55 \pm 10$ mm, which is appropriate for the average user. The total volume of the device is ca. 5 cc.

A device of the foregoing type is substantially filled with a 25% (wt.) aqueous solution of the $C_{10}EO_5$ surfactant. Excess air is removed. The device is autoclaved and is ready for use as a vaginal contraceptive.

The device is folded and placed in the vagina posterior to the introitus in a manner such that the silicone membrane substantially covers the cervical os. The device is worn during the time between menses and safely and effectively delivers a spermicidal amount of $C_{10}EO_5$ surfactant to the vaginal area. In particular, the positioning and shape of the device bathes the cervical os with the spermicidal surfactant via the silicone membrane. The lobes and grooves provide radially distributed channels for the flow of menses and similar biological fluids around the device, obviating problems with fluid accumulation, odor, and infection. Substantially none of the surfactant migrates through the PE back into the general vaginal cavity. Thus, substantially all of the surfactant is delivered to the intended situs, i.e., the cervical os and immediate surrounding area. The device is quite comfortable and remains in place during ordinary muscular exertions.

In the device of Example II, the $C_{10}EO_5$ surfactant is replaced by an equivalent amount of $C_{10}EO_6$ surfactant and excellent spermicidal results are secured.

EXAMPLE III

A disc-shaped silicone device as depicted in FIG. 8 is prepared in the manner described hereinabove by appropriate selection of die configuration and assembly of individual "segments". The device has the general dimensions of the device of Example I, with the exception that the container formed by the membranes is discoid, rather than dish-shaped.

The back of the disc comprises silicone rubber reinforced by the internal walls formed by bonding the segments together as shown in FIG. 9. The front half of the disc comprises silicone rubber ca. 0.15 cm thick.

The disc-shaped device is substantially filled with a 50% (wt.) aqueous solution of the $C_{10}EO_5$ spermicidal surfactant. Excess air is removed. The device is sterilized and packaged in the manner described hereinabove and is ready for use as a vaginal contraceptive.

The device is folded and placed in the vagina posterior to the introitus. The disc opens by virtue of the rigidity imparted by the inner reinforcing walls, and the inner silicone membrane is placed in the closest possible proximity to the cervical os. The device is worn during the time between menses and safely and effectively delivers monomers of the spermicidal surfactant to the vaginal area during that time. The device is quite comfortable and remains in place during intercourse.

The device of Example III is prepared using synthetic rubber and excellent spermicidal results are secured.

The device of Example III is prepared from the following polymeric materials: silicone/polycarbonate copolymer; styrene/butadiene block copolymers; and ethylene-vinylacetate copolymers, said polymeric materials being used in combination with both $C_{10}EO_5$ and $C_{10}EO_6$. Excellent spermicidal results are secured.

What is claimed is:

1. A contraceptive device especially adapted for use within the vaginal cavity, comprising: a circumferentially lobed dish-shaped container, said container being formed from: a dish-shaped, scalloped back, said back being characterized by one or more thickened, reinforced areas, and a circumferentially lobed front face capping said back, at least a portion of said front face being a non-porous semi-permeable membrane transport surface; said container being substantially filled with an aqueous solution of a micelle-forming spermicidal surfactant compound at a concentration greater than or equal to the critical micelle concentration of said surfactant compound.

2. A device according to claim 1 wherein the thickened, reinforced areas in the back are substantially radially distributed.

3. A device according to claim 2 wherein the transport surface extends substantially across the front face of the device.

4. A device according to claim 1 wherein the semipermeable membrane comprises a pharmaceutically-acceptable silicone polymer.

5. A device according to claim 4 wherein the silicone polymer is substantially free from color-forming curing agents.

6. A device according to claim 5 wherein the membrane has a thickness in the range of from about 0.02 mm to about 0.6 mm.

7. A device according to claim 6 wherein the container is partitioned by said reinforced areas into a plurality of closed compartments.

8. A device according to claim 1 wherein the spermicidal surfactant compound is a nonionic surfactant selected from ethylene oxide condensates of aliphatic alcohols and ethylene oxide condensates of alkyl phenols.

9. A device according to claim 8 wherein the surfactant compound is characterized by a critical micelle concentration of at most about $5 \times 10^{-3}$ Molar.

10. A device according to claim 9 wherein the surfactant compound is $C_{10}EO_5$, $C_{10}EO_6$, or mixtures thereof.

11. A contraceptive device especially adapted for use within the vaginal cavity, comprising a dish-shaped or disc-shaped container, said container being characterized by one or more internal reinforcing walls, said container being partitioned by said reinforcing walls into a plurality of compartments, said compartments containing an aqueous solution of a micelle-forming surfactant compound at a concentration greater than or equal to the critical micelle concentration of said surfactant compound, a portion of an external surface of said container being a non-porous, semi-permeable membrane transport surface.

12. A device according to claim 11 wherein the reinforcing walls in the container are substantially radially distributed.

13. A device according to claim 12 wherein the transport surface extends substantially across one face of the device.

14. A device according to claim 11 wherein the semipermeable membrane comprises a pharmaceutically-acceptable silicone polymer.

15. A device according to claim 14 wherein the silicone polymer is substantially free from color-forming curing agents.

16. A device according to claim 15 wherein the membrane has a thickness in the range of from about 0.02 mm to about 0.6 mm.

17. A device according to claim 11 wherein the spermicidal surfactant compound is a nonionic surfactant selected from ethylene oxide condensates of aliphatic alcohols and ethylene oxide condensates of alkyl phenols.

18. A device according to claim 17 wherein the surfactant compound is characterized by a critical micelle concentration of at most about $5 \times 10^{-3}$ Molar.

19. A device according to claim 18 wherein the surfactant compound is $C_{10}EO_5$, $C_{10}EO_6$, or mixtures thereof.

20. A device according to claim 1, comprising: a circumferentially lobed, dish-shaped silicone polymer container, said container being formed from: a thin, flexible, comfortable back having a scalloped periphery, the concave surface of the back being characterized by one or more radially distributed thickened, reinforced areas corresponding to the scalloped periphery; and a circumferentially lobed front face capping the back, the lobes in the front face being shaped to meet the scalloped periphery of the back when the front face and back are joined; a portion of the front face being a non-porous, semi-permeable membrane transport surface; said container being substantially filled with an aqueous solution of $C_{10}EO_5$, $C_{10}EO_6$, or mixture thereof.

* * * * *